(12) United States Patent
Lee et al.

(10) Patent No.: US 11,857,339 B2
(45) Date of Patent: Jan. 2, 2024

(54) HEADGEAR-TYPE DEVICE FOR HAZARDOUS AIR QUALITY WARNING AND AIR QUALITY IMPROVEMENT

(71) Applicant: LEESTECH SYSTEM CO.,LTD., Seoul (KR)

(72) Inventors: Jae Hong Lee, Seoul (KR); Soon Wi Kim, Seoul (KR); Won Sik Lee, Seoul (KR); Hyun Sik Lee, Seoul (KR); Na Young Lee, Seoul (KR); Soon Hyang Lee, Seoul (KR)

(73) Assignee: LEESTECH SYSTEM CO., LTD., Seoul (KR)

( * ) Notice: Subject to any disclaimer, the term of this patent is extended or adjusted under 35 U.S.C. 154(b) by 7 days.

(21) Appl. No.: 17/633,206

(22) PCT Filed: Aug. 6, 2020

(86) PCT No.: PCT/KR2020/010416
§ 371 (c)(1),
(2) Date: Feb. 6, 2022

(87) PCT Pub. No.: WO2021/025492
PCT Pub. Date: Feb. 11, 2021

(65) Prior Publication Data
US 2022/0330905 A1   Oct. 20, 2022

(30) Foreign Application Priority Data
Aug. 6, 2019   (KR) .......................... 10-2019-0095352

(51) Int. Cl.
*A61B 5/00*    (2006.01)
*A61B 5/0205*  (2006.01)
(Continued)

(52) U.S. Cl.
CPC ........ *A61B 5/6803* (2013.01); *A61B 5/02055* (2013.01); *A61B 5/6814* (2013.01);
(Continued)

(58) Field of Classification Search
CPC ..... A61B 5/00; A61B 5/0205; A61B 5/02055; A61B 5/04; A61B 5/0476; A61B 5/11;
(Continued)

(56) References Cited

U.S. PATENT DOCUMENTS

| 2004/0064169 A1* | 4/2004 | Briscoe ..................... A61F 7/10 607/104 |
| 2016/0113580 A1 | 4/2016 | Park et al. |

(Continued)

FOREIGN PATENT DOCUMENTS

| JP | 5930155 B2 | 6/2016 |
| KR | 10-0786279 B1 | 12/2007 |

(Continued)

OTHER PUBLICATIONS

NPL Search (Apr. 7, 2023).*

*Primary Examiner* — Van T Trieu
(74) *Attorney, Agent, or Firm* — Maschoff Brennan

(57) ABSTRACT

Disclosed is a headgear-type device for hazardous air quality warning and air quality improvement, wherein the device can collect biometric information of a worker, wired and wireless communications, and information about the quality of outside air around the worker so as to warn the worker of a hazard or improve air quality at the site. The headgear-type device for hazardous air quality warning and air quality improvement according to the present invention may comprise: a headgear-type biometric sensor which comes into close contact with the head of the worker so as to sense biometric information of the worker and thus allow measurements of the worker's physical conditions; a terminal
(Continued)

which is wiredly or wirelessly connected to the headgear-type biometric sensor so as to transmit and receive the biometric information; and a server which receives the biometric information from the terminal, calculates, on the basis thereof, whether the biometric information is in a normal condition range, according to a program, and when the biometric information is not in the normal condition range, issues a warning to the worker by transmitting a warning state to the terminal.

8 Claims, 6 Drawing Sheets

(51) Int. Cl.
*H04W 4/90* (2018.01)
*H04W 4/80* (2018.01)
*A62B 7/12* (2006.01)
*A62B 9/00* (2006.01)
*A62B 18/02* (2006.01)
*G08B 21/12* (2006.01)

(52) U.S. Cl.
CPC ............ *A61B 5/7275* (2013.01); *A61B 5/746* (2013.01); *A62B 7/12* (2013.01); *A62B 9/006* (2013.01); *A62B 18/02* (2013.01); *G08B 21/12* (2013.01); *H04W 4/80* (2018.02); *H04W 4/90* (2018.02)

(58) Field of Classification Search
CPC ....... A61B 5/1455; A61B 5/18; A61B 5/6814; A61B 5/7275; A61B 5/746; A61B 5/6803; G08B 21/04; G08B 21/12; A62B 7/12; A62B 9/00; H04N 7/14; H04N 7/142
See application file for complete search history.

(56) References Cited

U.S. PATENT DOCUMENTS

| | | | |
|---|---|---|---|
| 2016/0296720 A1* | 10/2016 | Henry | A61M 16/0875 |
| 2019/0167211 A1* | 6/2019 | Everman | G09B 9/08 |
| 2019/0175411 A1 | 6/2019 | Awiszuz et al. | |
| 2019/0232013 A1* | 8/2019 | Yu | A61B 5/6819 |
| 2020/0261009 A1* | 8/2020 | Everman | G16H 40/67 |

FOREIGN PATENT DOCUMENTS

| | | |
|---|---|---|
| KR | 10-1422234 B1 | 7/2014 |
| KR | 10-2016-0074435 A | 6/2016 |
| KR | 10-1948151 B1 | 2/2019 |
| KR | 10-2019-0022685 A | 3/2019 |
| KR | 10-2090730 B1 | 3/2020 |

* cited by examiner

[FIG. 1]
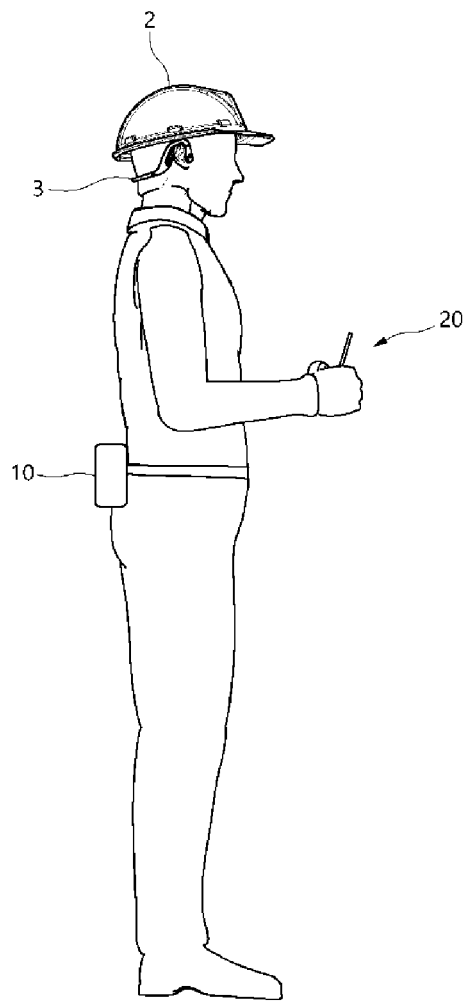
[FIG. 2]
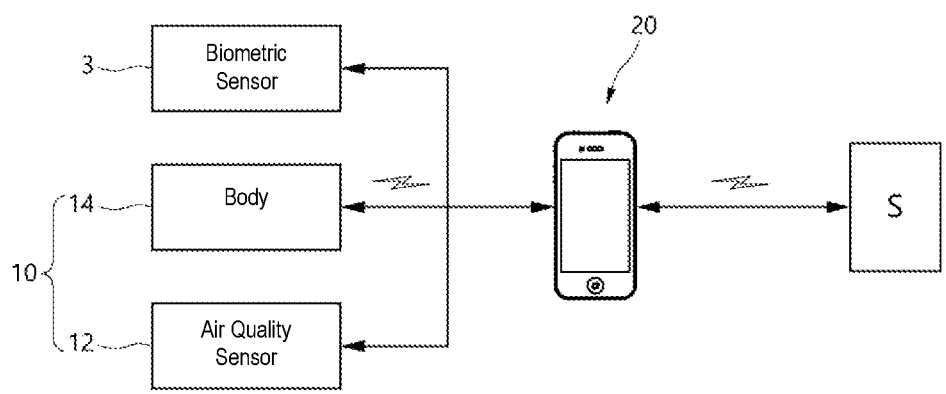

[FIG. 3]
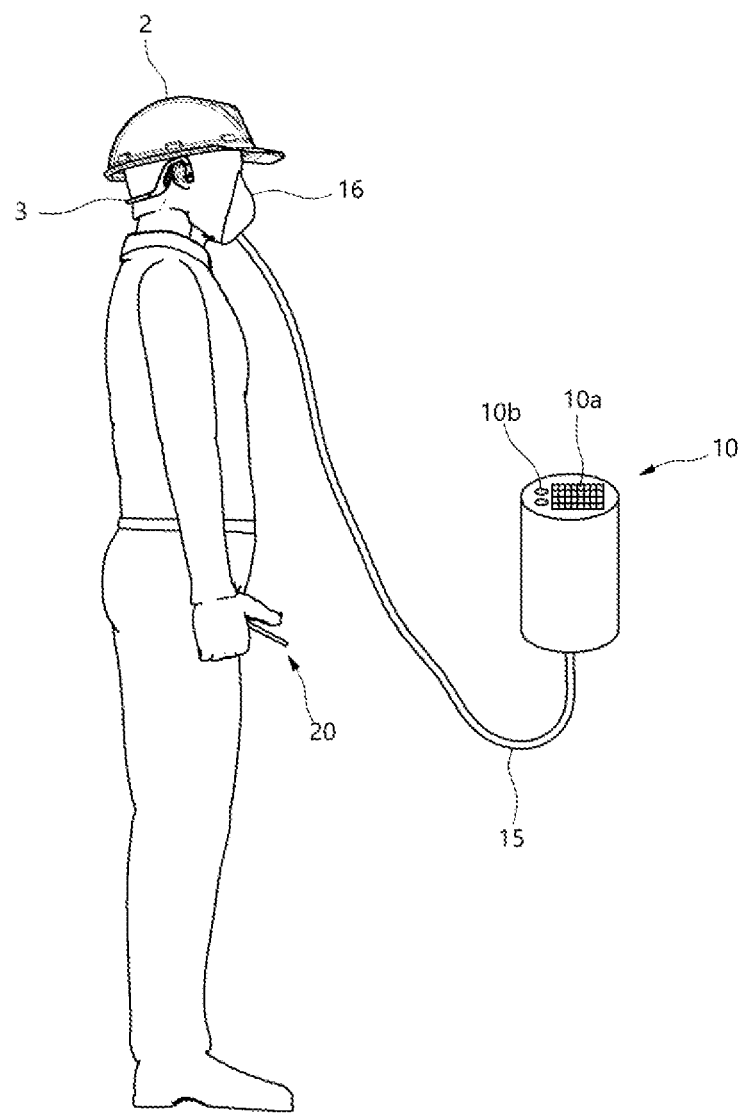

[FIG. 4]
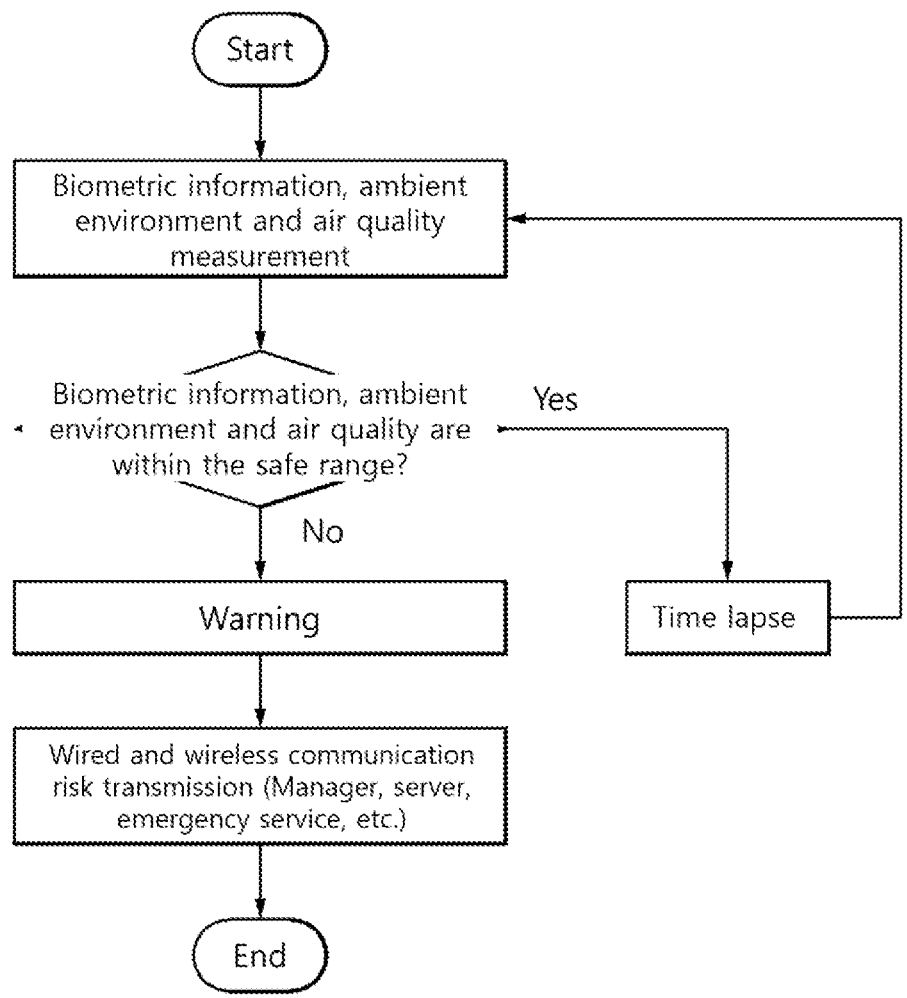

[FIG. 5]
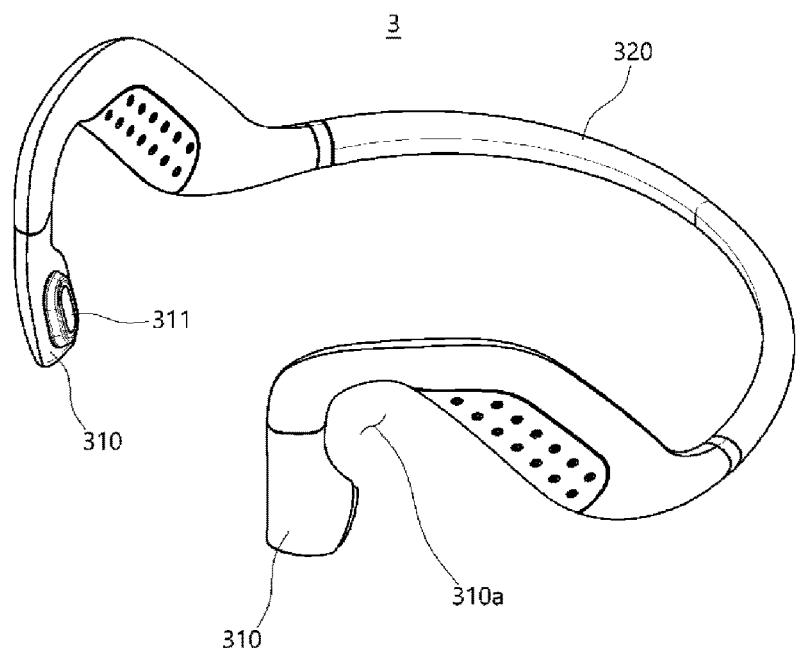
[FIG. 6]
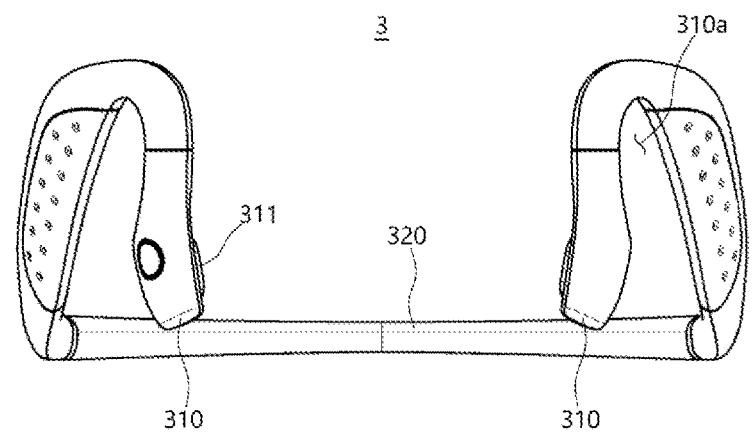

[FIG. 7]
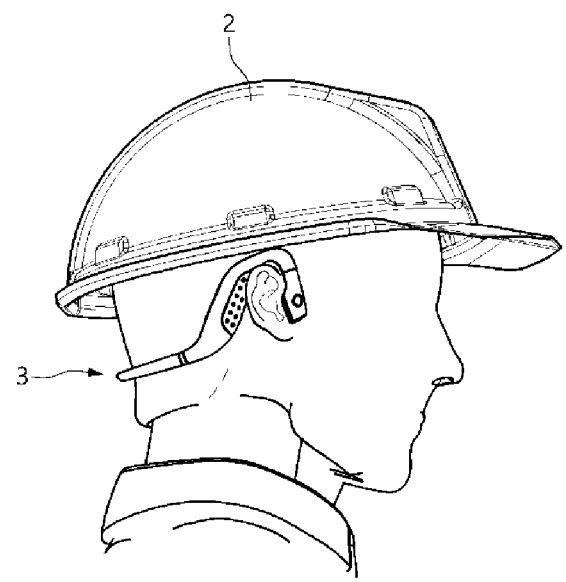
[FIG. 8]
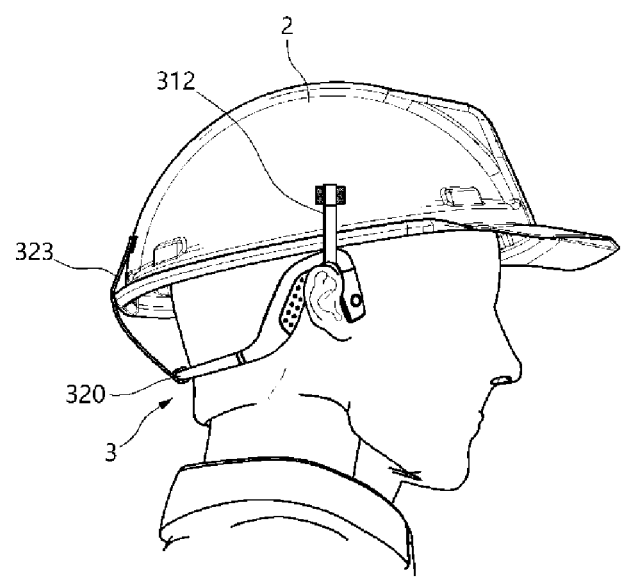

[FIG. 9]
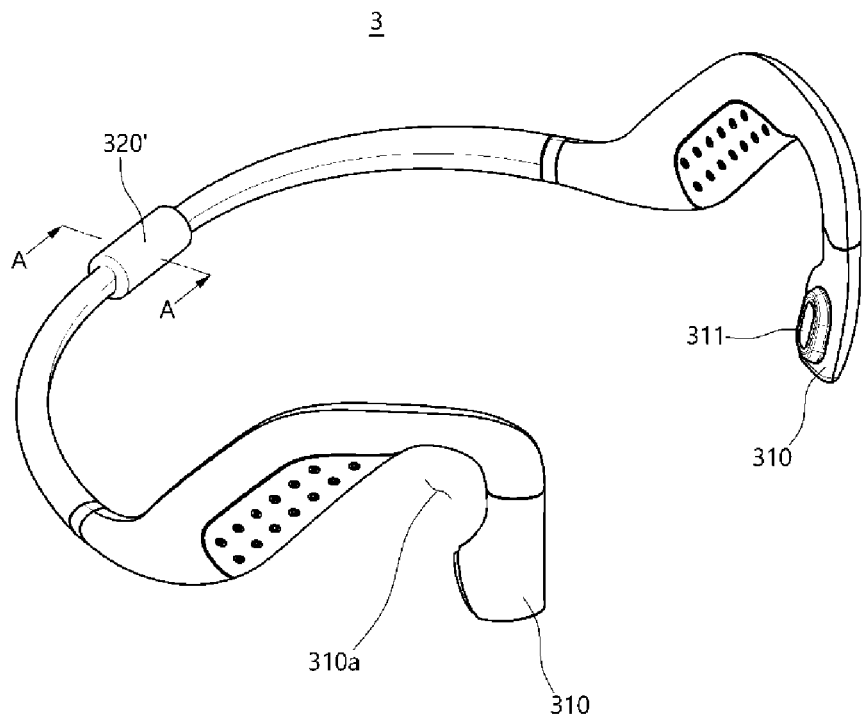
[FIG. 10]
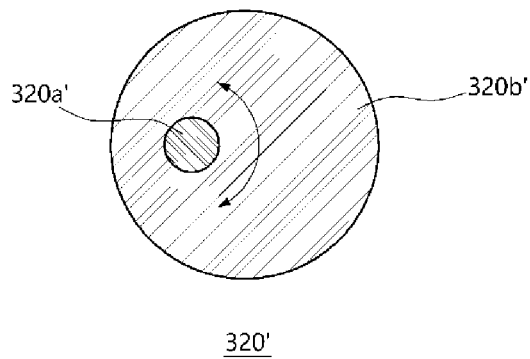

HEADGEAR-TYPE DEVICE FOR HAZARDOUS AIR QUALITY WARNING AND AIR QUALITY IMPROVEMENT

TECHNICAL FIELD

The present invention relates to a headgear-type device for hazardous air quality warning and air quality improvement, wherein the device can collect biometric information of a worker and information about the quality of outside air around the worker so as to warn the worker of a hazard or improve air quality at the site.

BACKGROUND ART

In general, as human civilization develops, research or work is frequently conducted in dangerous environments such as underground, underwater, in the jungle, in the severe hot region, or in the severe cold region. In addition, the work is frequently conducted at the site of a fire or radiation leak.

In this case, there is a risk that workers may lose consciousness due to toxic gas, heat, or cold. Since these risk factors are difficult to identify with the naked eyes, it is also difficult for the workers to easily recognize a hazardous situation until the workers are subject to the danger. In addition, even if a plurality of workers work together, it is difficult to quickly grasp the dangers of fellow workers because visibility cannot be secured due to smoke or darkness. For this reason, workers who work in a manhole, a fire site, a nuclear reactor, etc. often lose their lives.

Various safety devices are provided to prevent such accidents, but safety devices cannot always be used due to limitations such as working speed or working environment. Therefore, the need for a technology that can prevent danger by checking the user's condition or surrounding environment even at a hazardous site has emerged.

In this regard, Korean Patent No. 10-1422234 has suggested an emergency situation notice system using biometric and GPS information, which recognizes biometric information including heartbeat, pulse, body temperature, and vibration, and has a GPS reception function to receive the current location from a notification device and a mobile phone, a couple interworking function consisting of two or more detachable ring structures, and a notification device in the form of a bracelet wearable to a wrist of a user, wherein if any of the biometric information exceeds the preset threshold, a notification is immediately sent to a preset guardian.

However, according to Korea Patent No. 10-1422234, the occurrence of an emergency is unconditionally notified when any one of the biometric information exceeds the preset threshold. That is, it may be frequently happen that one of heartbeat, pulse, body temperature, and vibration may have abnormal values due to the ambient environment around the user although the physical condition of the user is normal. However, this event cannot be considered at all, and accordingly, there is a problem that the reliability of the dangerous situation notification operation is lowered.

DISCLOSURE

This patent application claims the benefit of and priority to App. No. KR 10-2019-0095352 filed Aug. 6, 2019, titled HEADGEAR-TYPE DEVICE FOR HAZARDOUS AIR QUALITY WARNING AND AIR QUALITY IMPROVEMENT, which is incorporated in the present disclosure by reference in its entirety.

Technical Problem

The present invention has been made to solve the above problem, and an object of the present invention is to provide a headgear-type device for hazardous air quality warning and air quality improvement, which collects air quality information around the working environment and biometric information of a worker in real time, transmits the biometric information to a server through wireless communication, analyzes the biometric information, and when a dangerous situation is detected, informs a worker of the dangerous situation to allow the worker to take a necessary step against the dangerous situation, and at the same time, makes an emergency call to rescue the worker.

Technical Solution

In order to accomplish the above object, the present invention provides a headgear-type device for hazardous air quality warning and air quality improvement, in which the headgear-type device includes: a headgear-type wired/wireless communication and health-bio biometric sensor which comes into close contact with a face or a head of a worker to detect biometric information of the worker in order to measure a body condition of the worker; a terminal which is wirelessly connected to the headgear-type wired/wireless communication and health-bio biometric sensor to receive the biometric information; and a server which receives the biometric information from the terminal, calculates whether the biometric information is in a normal condition range according to a program based on the biometric information, and issues a warning by transmitting a warning state to the terminal when the biometric information is not in the normal condition range.

The headgear-type device may further include an air quality sensor for sensing air quality to obtain air quality information around the worker, and transmitting the air quality information to the terminal.

The headgear-type device may further include a portable air purifier operated to purify air around the worker when a warning state is transmitted from the server to the terminal.

The portable air purifier may be attached to a part of a body of the worker such that the portable air purifier is carried and fixed.

The portable air purifier may include a mask directly connected to a mouth of the worker to allow purified air to be supplied to the mouth of the worker, and a hose connecting the mask and a body of the portable air purifier.

The portable air purifier may be provided with a handle so that the worker is able to hold the portable air purifier using a hand, and a mask that is worn over a mouth and a nose is fixed to an exhaust port formed in a fixing device to discharge the purified air.

The headgear-type biometric sensor may be a pulse oximeter that detects oxygen saturation of blood, which is one of biometric information, while making close contact with a skin of the head.

The headgear-type biometric sensor may be a pulse signal that detects a pulse of blood, which is one of biometric information, while making close contact with a skin of the head.

The headgear-type biometric sensor may be a temperature sensor that detects a temperature of a human body, which is one of biometric information, while making close contact with a skin of the head.

The headgear-type biometric sensor may be a proximity sensor that detects a close-fitting body and other signals, which is one of biometric information, while making close contact with a skin of the head.

Each of the headgear-type biometric sensor and the air quality sensor may be driven by an independent constant power source or a battery.

The headgear-type biometric sensor may include: a case including both end portions configured to come into close contact with both ears of the body of the worker by an elastic force at a position near the both ears of the body of the worker, a mounting portion extending from the both end portions to be caught on the ears; and an extension portion extending from the mounting portion such that both ends thereof meet with each other at a back of the head and providing an elastic force to the both end portions; and an oxygen saturation biometric sensor installed at the both end portions of the case to detect oxygen saturation which a is health-bio biometric signal of the worker.

The headgear-type biometric sensor may include: a case including both end portions configured to come into close contact with both ears of the body of the worker by an elastic force at a position near the both ears of the body of the worker, a mounting portion extending from the both end portions to be caught on the ears; and an extension portion extending from the mounting portion such that both ends thereof meet with each other at a back of the head and providing an elastic force to the both end portions; and a wired/wireless sound and data device installed at the both end portions of the case.

The headgear-type device may further include at least one connecting line configured to connect the case and a working hat of the worker each other in order to distribute a load of the headgear-type biometric sensor.

The extension portion may be provided with a linear shaft formed along the extension portion to adjust an adhesion part of the health-bio biometric sensor, and a cylindrical adjustment portion eccentrically and rotatably installed on the linear shaft.

Advantageous Effects

According to the present invention as described above, the following effects are obtained.
(1) The present invention can provide an effect of saving lives by alerting workers to evacuate in real time when an abnormality occurs in the body or pollution of ambient air is detected in a hazardous workplace.
(2) The present invention can ensure the work safety by allowing workers to evacuate when air in the workplace is polluted, and at the same time, can purify ambient air to allow the workers to inhale the purified air while evacuating.

DESCRIPTION OF DRAWINGS

FIG. 1 is a side view of a worker wearing a health-bio headgear-type device for hazardous air quality warning and air quality improvement according to the present invention.

FIG. 2 is a block diagram showing a configuration of a health-bio headgear-type device for hazardous air quality warning and air quality improvement according to the present invention.

FIG. 3 is a side view in case of an emergency of a worker wearing a health-bio headgear-type device for hazardous air quality warning and air quality improvement according to the present invention, FIG. 4 is a flowchart for operating a headgear-type device for hazardous air quality warning and air quality improvement according to the present invention.

FIG. 5 is a perspective view of a headgear-type biometric sensor, which is a part of a headgear-type device for hazardous air quality warning and air quality improvement according to the present invention.

FIG. 6 is a front view of a headgear-type wired/wireless communication and health-bio biometric sensor, which is a component of a headgear-type device for hazardous air quality warning and air quality improvement according to the present invention.

FIG. 7 is a side view showing a worker wearing a headgear-type wired/wireless communication and health-bio biometric sensor, which is a component of a headgear-type device for hazardous air quality warning and air quality improvement according to the present invention.

FIG. 8 is a side view showing a worker wearing a headgear-type wired/wireless communication and health-bio biometric sensor, which is a component of a headgear-type device for hazardous air quality warning and air quality improvement according another embodiment of the present invention.

FIG. 9 is a perspective view of a headgear-type wired/wireless communication and health-bio biometric sensor, which is a component of a headgear-type device for hazardous air quality warning and air quality improvement according another embodiment of the present invention.

FIG. 10 is a sectional view taken along line AA shown in FIG. 9.

BEST MODE

Mode for Invention

Hereinafter, embodiments of the present invention will be described in detail with reference to the accompanying drawings so that those skill in the art can easily implement the present invention. The present invention may be embodied in many different forms and is not limited to the embodiments described herein. In order to clearly explain the present invention, parts irrelevant to the description are omitted in the drawings, and the same reference numerals are assigned to the same or similar components throughout the specification.

In the specification, terms such as "comprises" or "have" are intended to designate the existence of features, numbers, steps, operations, components, parts, or combinations thereof described in the specification, and it should be understood that the existence or addition of the other features, numbers, steps, operations, components, parts or combinations thereof is not precluded in advance. Also, when a part of a layer, film, region, plate, etc. is said to be "on" another part, this includes not only the case where the other part is "directly on", but also the case where there is another part therebetween. Conversely, when a part of a layer, film, region, plate, etc. is said to be "under" another part, this includes not only cases where it is "directly under" another part, but also a case where there is another part therebetween.

Hereinafter, a device for a hazardous air quality warning and air quality improvement according to an embodiment of the present invention will be described in more detail with reference to the drawings.

Referring to FIGS. 1 to 8, a headgear-type device for hazardous air quality warning and air quality improvement according to a first embodiment of the present invention may include a headgear-type wired/wireless communication and health-bio biometric sensor 3, a terminal 20, a server (S), an air quality sensor 12, and a portable air purifier 10.

Referring to FIGS. 1 to 7, the headgear-type wired/wireless communication and health-bio biometric sensor 3 may detect biometric information so as to measure the state of the worker's body in close contact with the worker's head.

In this case, the headgear-type wired/wireless communication and health-bio biometric sensor 3 may be installed to be in close contact with the worker's head within 10 cm outside the ear to measure oxygen saturation of the corresponding part. In particular, since blood vessels pass in front of the ear, the bio-signal may be obtained by making close contact with the target.

In this case, the headgear-type wired/wireless communication and health-bio biometric sensor 3 may include a pulse oximeter for detecting oxygen saturation of blood, which is one of biometric information.

In this case, the pulse oximeter may be used for a non-vascular measurement of oxygen saturation in blood by applying light of two different wavelengths from a semiconductor device to a blood vessel, and may be very useful because it has less invasiveness and quick response to the patient.

In this case, the headgear-type biometric sensor may be a pulse signal sensor for detecting a pulse of blood, which is one of biometric information, while making close contact with the skin of the head.

In this case, the headgear-type biometric sensor may be a temperature sensor that detects a body temperature, which is one of biometric information, while making close contact with the skin of the head.

In this case, the headgear-type biometric sensor may be a proximity sensor that detects a close-fitting body and other signals, which are one of biometric information, while making close contact with the skin of the head.

In this case, referring to FIGS. 5 to 7, the headgear-type wired/wireless communication and health-bio biometric sensor 3 may include cases 310 and 320, and health-bio oxygen saturation sensor 311.

In this case, the cases 310 and 320 may have both end portions 310 formed at symmetrical positions in the vicinity of both ears of the worker's body to make close contact with the ears by elastic force, a mounting portion 310a extending from the both end portions 310 to be caught on the ears, and an extension portion 320 extending from the mounting portion 310a to meet each other at the back of the head while providing elastic force to the both end portions.

In this case, the health-bio oxygen saturation sensor 311 may be installed at both end portions 310 of the cases 310 and 320 to detect the oxygen saturation of the worker.

In this case, the basic electronic components are mounted inside the case 310 and 320 of the headgear-type wired/wireless communication and health-bio biometric sensor 3. That is, a battery and a PCB are basically mounted, and related electronic components may also be mounted to transmit and receive signals wirelessly with respect to the terminal.

In this case, the headgear-type wired/wireless communication and health-bio biometric sensor 3 may transmit and receive data through wired/wireless communication with respect to basic electronic components, and speakers and microphones used for communication may be mounted inside the cases 310 and 320.

In this case, the headgear-type wired/wireless communication and health-bio biometric sensor 3 may have a power switch, an LED, etc. which are exposed on the outer surface of the case 310 and 320 to notify the operating state and abnormality of the biometric signal of the worker, as needed.

In this case, in the headgear-type wired/wireless communication and health-bio biometric sensor 3, both end portions 310 may come into close contact with the measurement position by the elastic force of the cases 310 and 320, the mounting portion 310a of the cases 310 and 320 may be caught on the ear, and the extension portion 320 may be caught on the back of the worker's head, so that the sensing operation may be performed in a state in which the biometric sensor is firmly fixed to the body during the operation of the worker.

In this case, the headgear-type wired/wireless communication and health-bio biometric sensor may be equipped with other sensors including heart rate, pulse, body temperature, vibration, and position sensors, in addition to the oxygen saturation sensor to detect biometric information.

Referring to FIGS. 1 to 3, the terminal 20 may be connected to the headgear-type wired/wireless communication and health-bio biometric sensor 3 by wired or wireless manner to receive biometric information.

In this case, a dedicated terminal may be used as the terminal 20, or a corresponding application may be installed in smart phones which are widely used in these days.

The server S may receive the biometric information from the terminal 20, calculate whether it is within the normal state range according to the program based on the biometric information, and send a warning state to the terminal when the biometric information is out of the normal state range.

Referring to FIGS. 1 to 3, the air quality sensor 12 may detect air quality to obtain air quality information around the worker, and transmit the air quality information to the terminal 20.

As shown in FIGS. 1 to 3, the portable air purifier 10 may be operated to purify the air around the worker when a warning state is received from the server S to the terminal 20.

In this case, the portable air purifier 10 may be attached to a part of the worker's body so that the portable air purifier 10 may be carried.

In this case, the portable air purifier 10 may include a hose 15 for connecting a mask 16 covering a mouth and a body 14 of the air purifier so that purified air can be directly supplied to the mouth of the worker.

In this case, the portable air purifier 10 may be provided with a handle so that the worker may hold the portable air purifier 10 using a hand, and a mask that covers the mouth may be fixed an exhaust port for discharging the purified air.

In this case, each of the headgear-type wired/wireless communication and health-bio biometric sensor 3 and the air quality sensor 12 may be driven by an independent constant power source or battery.

Referring to FIG. 4, the operation sequence of the device for hazardous air quality warning and air quality improvement according to the present invention is briefly illustrated.

Referring to FIG. 4, when the worker starts work at the work position, monitoring is started. That is, the worker operates the application of the terminal 20 and also operates the sensors 3 and 12 and the portable air purifier 10 at the same time.

When the worker's condition monitoring starts, the biometric information and air quality information are received in the terminal 20 in real time by the headgear-type wired/wireless communication and health-bio biometric sensor 3 and air quality sensor 12, and at the same time, the information from the terminal 20 is transmitted to the server S.

The server S calculates whether the worker's biometric information, surrounding air quality, and environmental data are within the safe range as pre-programmed.

In this case, if the calculated value is within the safe range, the server S allows again the measurement for the biometric information and air quality information after a predetermined time elapses, and if the value is the same, it continues to repeat the measurement to ensure the safety of the worker.

In this case, if the value calculated by the server S is out of the safe range, the server S warns the worker through the terminal 20 in various ways.

In addition to the warnings, it is also possible to mobilize a rescue team or to automatically make a call to a 911, a preset terminal or a device.

In addition, the air quality around the worker may be purified by controlling the portable air purifier 10 to operate, or referring to FIG. 3, the worker may wear the mask 16 in a state in which the hose 15 is connected to the exhaust port of the portable air purifier 10 and the mask 16 is connected to the hose 15 so that the worker can directly inhale the purified air.

Referring to FIG. 1 there is shown a state in which the worker starts work in the working field. By notifying the start of the work through the terminal 20, the surrounding situation monitoring is started. That is, the biometric information of the worker is received at regular intervals in real time by the wired/wireless communication and health-bio bio sensor 3, and at the same time, the surrounding air quality information is also collected. The air quality sensor 12 may be mounted on the portable air purifier 10 or worn by a worker in an independent form.

Referring to FIG. 2, the terminal 20 makes communications with the wired/wireless communication and health-bio biometric sensor 3, the air quality sensor 12, and the air purifier 10 through various communication methods such as Bluetooth, infrared ray, optical wire, and wireless communication. The terminal 20 can also receive and transmit control signals while communicating with the devices. The terminal 20 transmits and receives the mutual communication result and information to and from the server S, and receives and transmits an accurate control signal to and from the server S in order to transfer the information to the portable air purifier 10.

Referring to FIG. 3, when the information received from the headgear-type wired/wireless communication and health-bio biometric sensor 3 or the air quality sensor 12 is determined to be a warning and emergency state in the server S, it is transmitted to the worker through the terminal 20 so that the worker can evacuate from the contaminated workplace, or if the situation is very serious, the worker wears the mask 16 connected to the exhaust port of the portable air purifier 10 through the hose and evacuates. The portable air purifier 10 may be provided with a button 1a for automatic and manual operation and a display 10b showing various states.

Referring to FIGS. 5 and 6, there is shown the external appearance of the headgear-type wired/wireless communication and health-bio biometric sensor 3. The headgear-type wired/wireless communication and health-bio biometric sensor 3 may be configured such that the cases 310 and 320 may include both end portions 310, the mounting portion 310a, and the extension portion 320. The both end portions 320 may come into close contact with the outside of the blood vessels in front and rear of the ears, which are parts of the worker's face, by the elastic force of the cases 310 and 320, the mounting portions 310a are configured to be caught on the ears, which are parts of the face, respectively, and the extension portion 320 is connected to each other so as to be caught on the back of the worker's head. Therefore, when the worker holds the both end portions 310 of the headgear-type wired/wireless communication and health-bio biometric sensor 3 and spreads the both end portions 310 in close contact with the front of the ears, the headgear-type wired/wireless communication and health-bio biometric sensor 3 is in close contact with the face of the worker to detect the oxygen saturation level of the worker in real time, and the oxygen saturation level is transmitted to the terminal 20.

Referring to FIG. 7, both end portions 310 of the cases 310 and 320, that is, the both end portions provided in inner surfaces thereof with the oxygen saturation sensor 311 make close contact with a portion located in front of the ear. Since the portion serves as a path of blood vessels of a person, it is suitable to measure the oxygen saturation. In other words, since blood vessels pass within about 10 cm near the ear, the measurement may be possible by positioning the both end portions on any one location around the ear. In particular, since large blood vessels pass in front of the ears, it would be most desirable to place the both end portions in this area. In a state in which the both end portions 310 are caught on the mounting portion 310a, the both end portions 310 are kept in close contact with the worker, so that both hands are free and the operation of the worker is not affected at all.

Meanwhile, referring to FIG. 8, there is shown a headgear-type wired/wireless communication and health-bio biometric sensor 3 according to another embodiment of the present invention. Here, at least one connecting line 312 and 323 is further provided for connecting the cases 310 and 320 and the working hat of the worker to each other so as to distribute the load of the headgear-type wired/wireless communication and health-bio biometric sensor 3. That is, when the elastic force of the cases 310 and 320 and the mounting state of the mounting portion 310a become longer, the worker may feel pain in the ear, so the connecting lines 312 and 323 are configured to be detachable to the working hat 2 using Velcro tape. In this case, the load applied to the entire mounting portion 310a can be distributed, so that the worker can be prevented from feeling pain in the ear. In this case, the connecting lines 312 and 323 can be connected to and installed in the middle of both mounting portions 310a and the extension portion 320.

Meanwhile, referring to FIGS. 9 and 10, a headgear-type biometric sensor 3 according to another embodiment of the present invention is shown. Here, the extension portion 320' of the cases 310 and 320' may be provided with a linear shaft 320a' formed along the extension portion 320' so as to finely adjust the adhesion part of the wired/wireless communication and health-bio oxygen saturation sensor 311, and a cylindrical adjustment portion 320b' installed eccentrically and rotatably on the linear shaft 320a'. Referring to FIG. 10, since it is rotated eccentrically, the distance of the biometric sensor in close contact with the back of the head may be finely adjusted, and eventually, the both end portion 310 may be finely adjusted in the front-rear directions. That is, if the sensing is not performed well, the adjustment portion 320b' may be rotated to finely adjust the sensing position so that the sensing may be achieved more accurately.

Although one embodiment of the present invention has been described above, the idea of the present invention is not limited to the embodiments presented in this specification, and those skilled in the art who understand the idea of the present invention can configure, within the scope of the same idea, that other embodiments may be easily proposed by adding, changing, deleting, or adding components, and this will also fall within the scope of the present invention.

INDUSTRIAL APPLICABILITY

The present invention can be used as a safety device when working in a closed space such as underground.

The invention claimed is:

1. A headgear-type device for hazardous air quality warning and air quality improvement, the headgear-type device comprising:
   a headgear-type wired/wireless communication and health-bio biometric sensor which comes into close contact with a face or a head of a worker to detect biometric information of the worker in order to measure a body condition of the worker;
   a terminal which is wirelessly connected to the headgear-type wired/wireless communication and health-bio biometric sensor to receive the biometric information; and
   a server which receives the biometric information from the terminal, calculates whether the biometric information is in a normal condition range according to a program based on the biometric information, and issues a warning by transmitting a warning state to the terminal when the biometric information is not in the normal condition range,
   wherein the headgear-type wired/wireless communication and health-bio biometric sensor is a biometric sensor equipped with a health-bio biometric sensor that detects biometric information while making close contact with a skin of the face or the head and provided with other sensors including heart rate, pulse, body temperature, vibration, and position sensors as well as an oxygen saturation sensor for sensing the biometric information,
   wherein the headgear-type wired/wireless communication and health-bio biometric sensor includes: a case including both end portions configured to come into close contact with both ears of the body of the worker by an elastic force at a position near the both ears of the body of the worker, a mounting portion extending from the both end portions to be caught on the ears; and an extension portion extending from the mounting portion such that both ends thereof meet with each other at a back of the head and providing an elastic force to the both end portions; and a wired/wireless communication and health-big oxygen saturation sensor installed at the both end portions of the case to detect state oxygen saturation with a wired/wireless communication and health-big sensor of the worker, and
   wherein the extension portion is provided with a linear shaft formed along the extension portion to adjust an adhesion part of the health-bio biometric oxygen saturation sensor, and a cylindrical adjustment portion eccentrically and rotatably installed on the linear shaft.

2. The headgear-type device of claim 1, further comprising an air quality sensor for sensing air quality to obtain air quality information around the worker, and transmitting the air quality information to the terminal.

3. The headgear-type device of claim 1 or 2, further comprising a portable air purifier operated to purify air around the worker when a warning state is transmitted from the server to the terminal.

4. The headgear-type device of claim 3, wherein the portable air purifier is attached to a part of a body of the worker such that the portable air purifier is carried and fixed.

5. The headgear-type device of claim 4, wherein the portable air purifier includes a mask directly connected to a mouth of the worker to allow purified air to be supplied to the mouth of the worker, and a hose connecting the mask and a body of the portable air purifier.

6. The headgear-type device of claim 4, wherein the portable air purifier is provided with a handle so that the worker is able to hold the portable air purifier using a hand, and a mask that is worn over a mouth and a nose is fixed to an exhaust port formed in a fixing device to discharge the purified air.

7. The headgear-type device of claim 2, wherein each of the headgear-type wired/wireless communication and health-bio biometric sensor and the air quality sensor is driven by an independent constant power source or a battery.

8. The headgear-type device of claim 1, further comprising at least one connecting line configured to connect the case and a working hat of the worker each other in order to distribute a load of the headgear-type wired/wireless communication and health-bio biometric sensor.

\* \* \* \* \*